United States Patent [19]

Hiraragi

[11] Patent Number: Plant 7,001

[45] Date of Patent: Aug. 29, 1989

[54] APPLE TREE: YATAKA

[75] Inventor: Tadao Hiraragi, Masuda, Japan

[73] Assignee: Makoto Okada, Hagashine, Japan

[21] Appl. No.: 938,399

[22] Filed: Dec. 5, 1986

[30] Foreign Application Priority Data

Dec. 5, 1985 [JP] Japan ..... 1707

[51] Int. Cl.[4] ..... A01H 5/00

[52] U.S. Cl. ..... Plt./34

[58] Field of Search ..... Plt. 34

[56] References Cited

U.S. PATENT DOCUMENTS

P.P. 5,086 8/1983 Carnefix ..... Plt. 34

P.P. 5,095 8/1983 Nicklin ..... Plt. 34

P.P. 5,937 4/1987 Morren-De Coster ..... Plt. 34

*Primary Examiner*—James R. Feyrer

*Attorney, Agent, or Firm*—Armstrong, Nikaido, Marmelstein, Kubovcik & Murray

[57] ABSTRACT

A new and distinct apple cultivar originating as a bud mutation of the Fuji apple tree, the Japanese leading late maturing apple cultivar. The new cultivar is generally similar to its parent, Fuji, with respect to branches, leaves and flowers, but the fruit is distinguished from the Fuji apple by coloring and maturing one month earlier than the parent.

4 Drawing Sheets

BACKGROUND OF THE INVENTION

The present invention relates to a new and distinct variety of apple tree given the denomination Yataka, and related to the known Fuji variety.

Fuji is a late maturing variety, which is picked in November to December. It would be desirable to pick Fuji apples at an earlier time of the year.

In September, 1982, the Applicant discovered a branch with some already colored fruit on a Fuji tree in his cultivated orchard (located at No. 24-6, Maetoriyama, Kameda, Kameda, Masuda machi, Hiraka gun, Akita prefecture, Japan). This fruit had colored and matured one month earlier than Fuji apples. At this time, the other fruit on the Fuji trees were still green.

The applicant thought that the early colored fruit was a new bud mutation of Fuji. In order to confirm the stability of the mutation with respect to coloring and maturing, the Applicant grafted the branch (including the new fruit variety) onto the original Fuji apple tree and 10 other mature trees of the Fuji variety (on Maruba rootstocks, i.e., Japanese common apple rootstocks) in his orchard. Continuous observation of the original sport and grafted bud mutation over 4 years has shown that its unique characteristics of early coloring and maturing are stable and are transmitted to top worked trees. In 1985, fruit borne by the grafted trees exhibited the same characteristics of earlier coloring and maturing as the originally discovered fruit of the new variety.

The new cultivar is generally similar to Fuji with respect to branches, leaves and flowers, but its fruit is distinguished from Fuji fruit by its early coloring and maturing.

The following is a detailed description of this new Yataka variety of apple tree.

BRIEF DESCRIPTION OF THE DRAWINGS

The accompanying photographs illustrate the invention and the characteristics of its fruit.

DESCRIPTION

Figure 1:
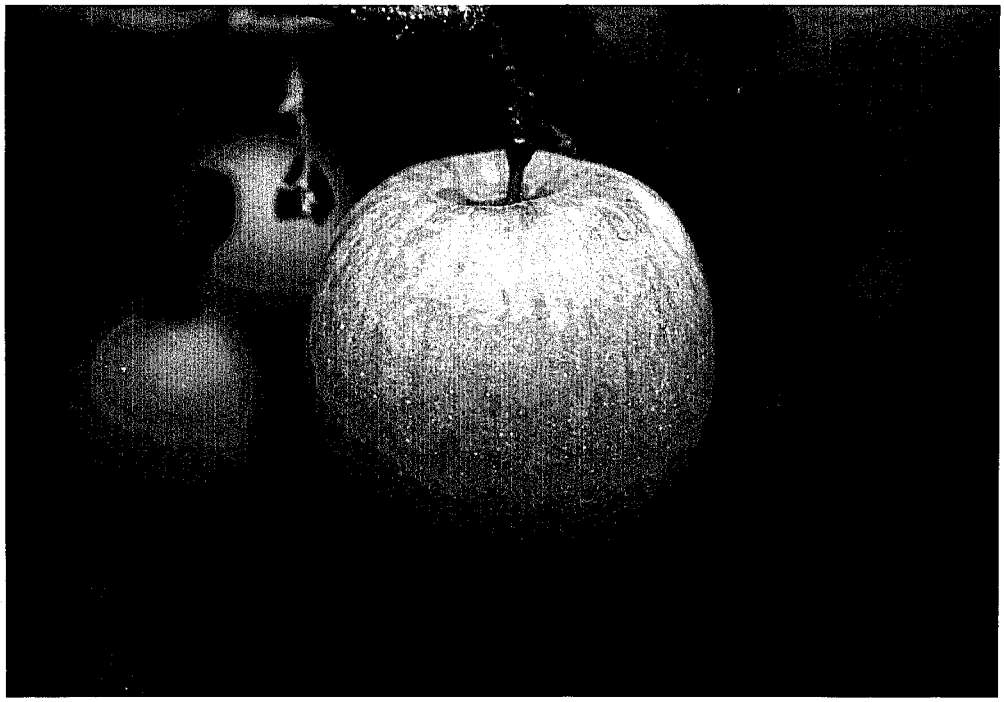
FIG. 1 is a photograph of a Yataka apple on the original tree.
Figure 2:
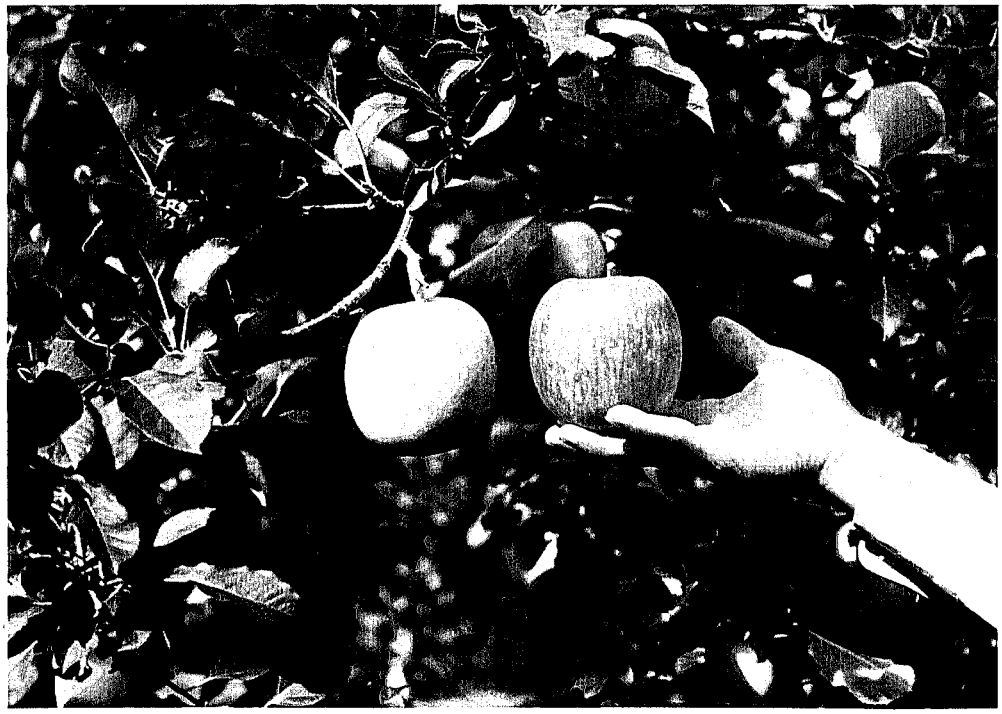
FIG. 2 is a photograph of a Yataka apple (right) compared to a Fuji apple (left).
Figure 3:
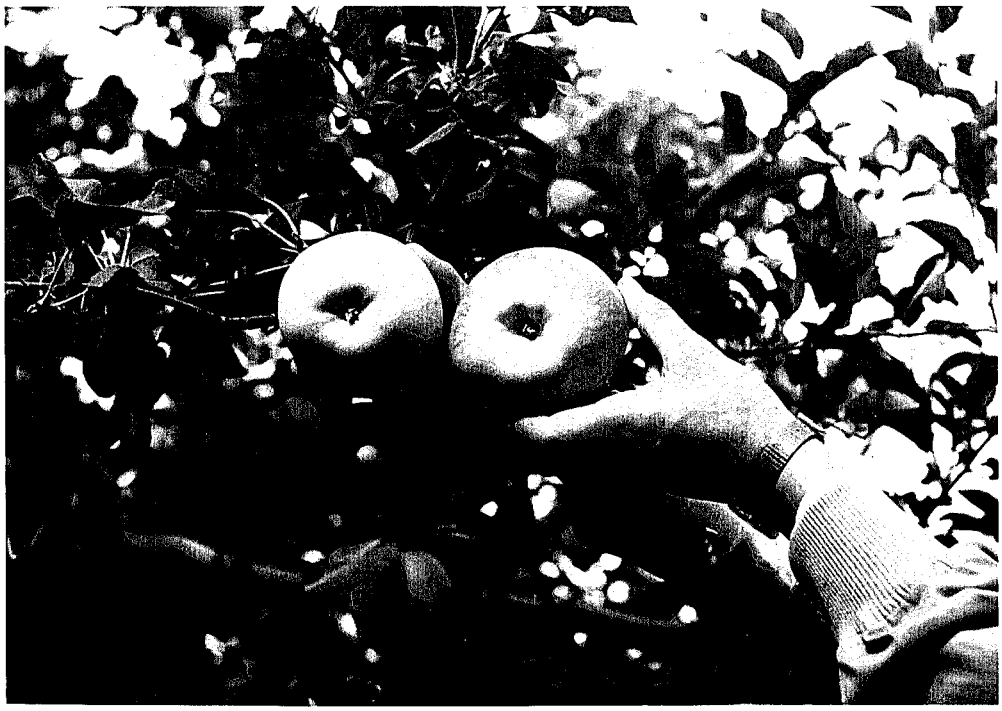
FIG. 3 is a photograph of a Yataka apple (right) compared to a Fuji apple (left).
Figure 4:
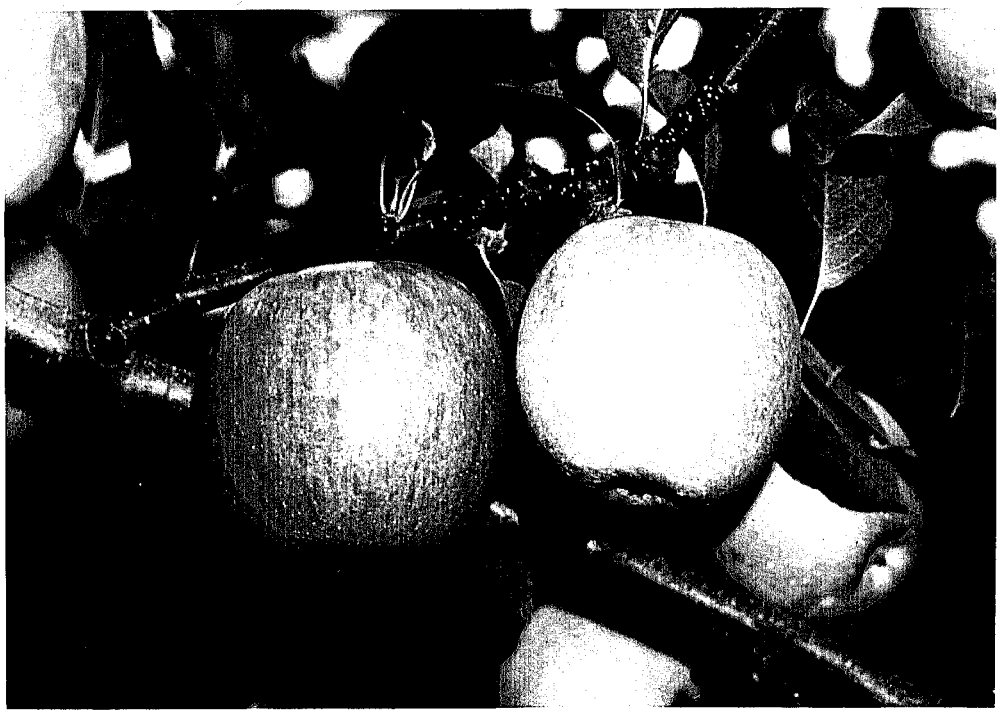
FIG. 4 is a photograph of a Yataka apple (left) compared to a Fuji apple (right).
Figure 5:
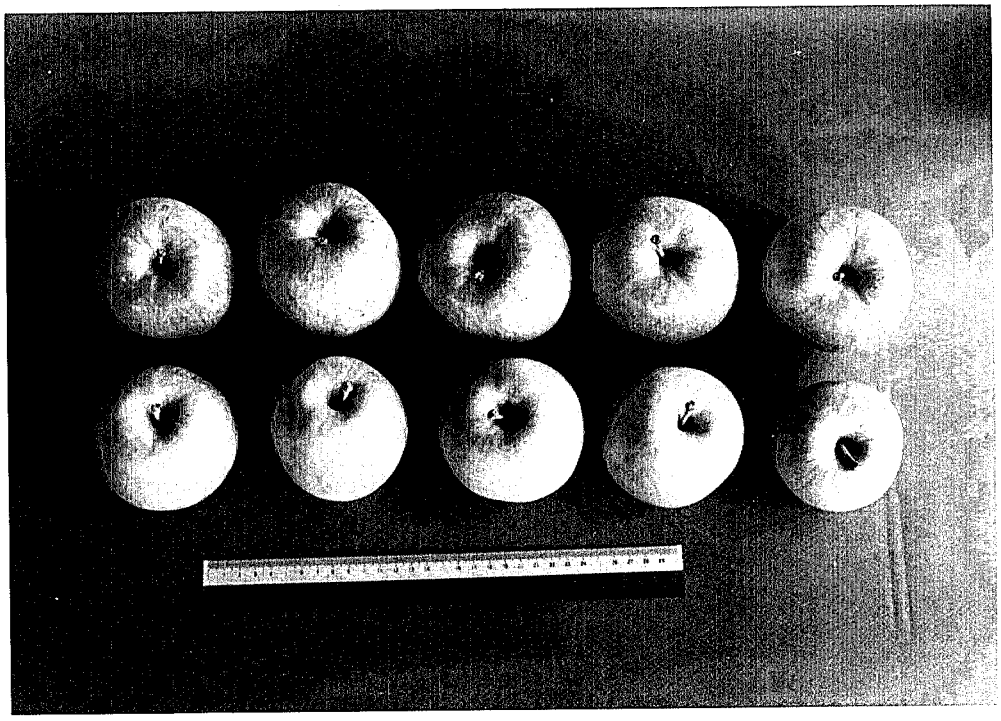
FIG. 5 is a photograph of Yataka apples (top) compared with Fuji apples (bottom).
Figure 6:
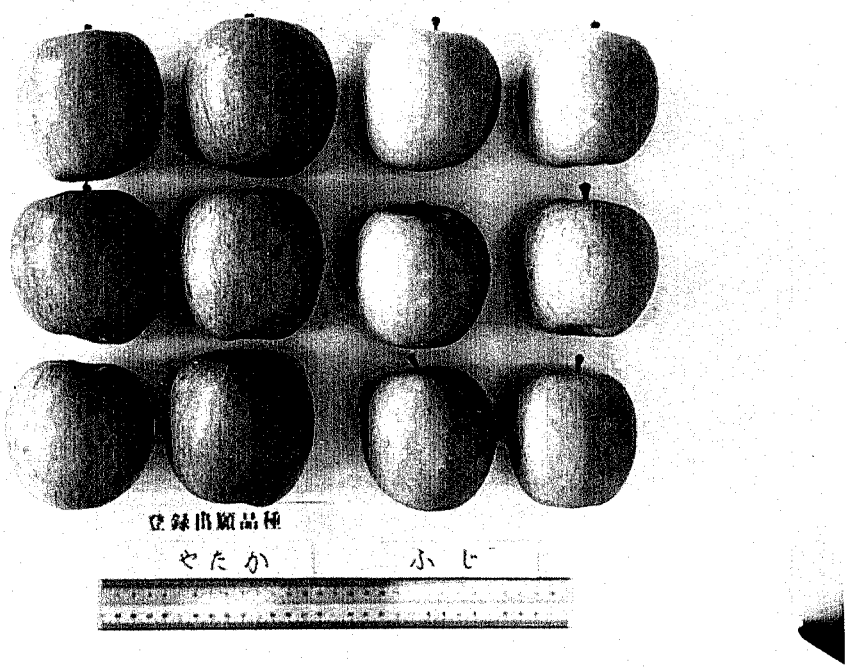
FIG. 6 is a photograph of Yataka apples (left two columns) compared to Fuji apples (right two columns).
Figure 7:
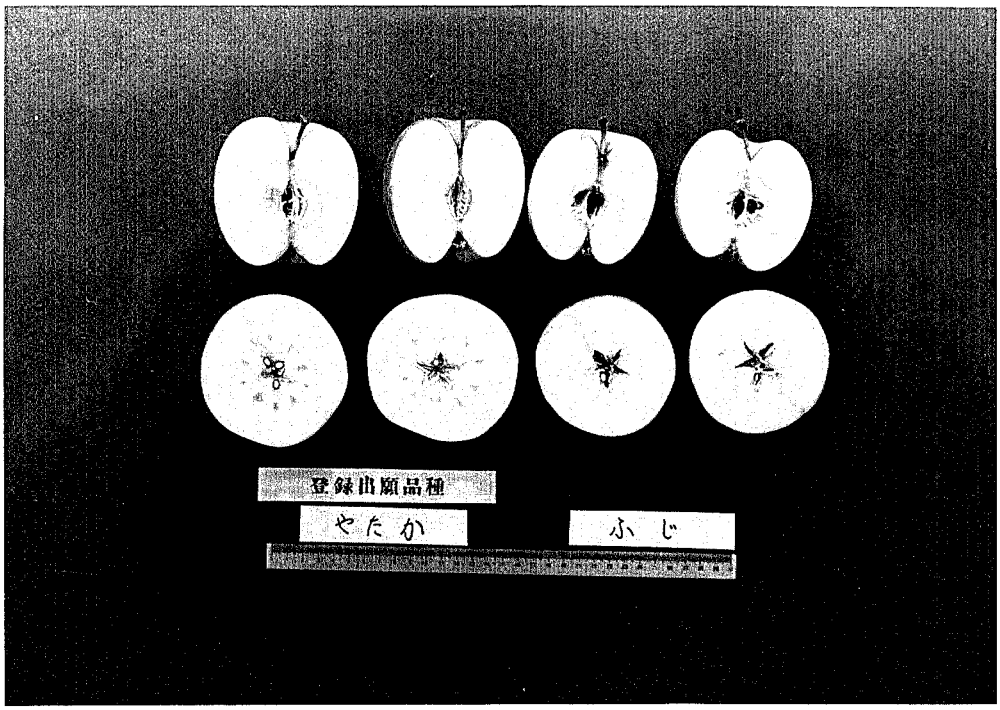
FIG. 7 is a photograph of the longitudinal and cross sections of Yataka apples (left two columns) compared to Fuji apples (right two columns).

A detailed description of the invention follows, with color terminology being given in accordance with the Munsell hue color chart.

A. Genus and species: *Malus pumila* (Mill)

B. Variety name: "Yataka"

C. Market type: An early coloring sport for the same market as the parent variety "Fuji", D. Tree: Tree is of medium vigor and tends to spread.

E. Shoot: Dormant shoot is brown (Munsell 5 YR 2/4) and slender with small and numerous lenticels. Pubescence on dormant one year old shoot is very slight. Internode is medium length.

F. Leaves: Leaf is small and green with serration. Length of leaf blade is 8.3 cm, width of leaf blade is 5.9 cm, petiole is short (2.5 cm) on one year tree. Leaf angle is wider than normal on new growth as well as spurs.

G. Flower: Time of flowering is medium. Flower is slightly cupped and medium size. Petal is round conical and L/B ratio is much longer than broad. Color of flower is white pale pink.

H. Fruit: Specimens described were grown at Akita, Japan. Maturing time, early October at Akita, Japan, one month earlier than Fuji, which matures early to late November.

*Size.*—Average 350 g, slightly larger than Fuji.

*Shape.*—Rounded, slightly longer than wide, and uniform. Both stem and blossom ends smoothly curved to about the same extent with shoulders and crown gently rounded, forming large, rounded fruit. Calyx is closed and basin is of medium depth and breadth. Cavity is deep and wide.

*Flesh.*—Flesh is creamy white, very juicy, firm and sweet. Flavor is good. Fruit is not easily bruised or browned. Texture is coarse. Well matured fruit has water core.

*Aroma.*—Mild.

*Skin.*—Ground color, yellowish green; surface color, red (Munsell 5R 5/12). Form of over color of skin, distinct strip. Skin is a little shiny and has medium lenticels. Skin has medium russet on the side. Surface bloom is scant allowing fruit to be polished to a waxy appearance.

*Core.*—Core is round and medium size.

*Seed.*—Oval and medium size.

I. Storage: Storage life at room temperature and colder temperature is extremely long. It can be stored for 4–5 months.

J. Fertilization: It exhibits low self fertilization and need pollinizer like Jonathan or Granny Smith, etc.

K. Productivity: It is productive and needs adequate fruit thinning.

*Usage.*—As dessert and processing apples.

*Conditions.*—Similar to growing conditions for Fuji.

I claim:

1. A new and distinct apple tree substantially as shown and described, particularly characterized by fruit which matures and colors earlier than the fruit of the known "Fuji" variety.

* * * * *